US010779517B2

(12) United States Patent
McCarthy et al.

(10) Patent No.: US 10,779,517 B2
(45) Date of Patent: Sep. 22, 2020

(54) ANIMAL WOUND MODEL AND METHODS OF USE

(71) Applicant: The Board of Regents of the University of Oklahoma, Norman, OK (US)

(72) Inventors: Cullen McCarthy, Oklahoma City, OK (US); William Berry, Edmond, OK (US); James Tomasek, Oklahoma City, OK (US); Jason Lees, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 108 days.

(21) Appl. No.: 16/068,492

(22) PCT Filed: Jan. 30, 2018

(86) PCT No.: PCT/US2018/015963
§ 371 (c)(1),
(2) Date: Jul. 6, 2018

(87) PCT Pub. No.: WO2018/144461
PCT Pub. Date: Aug. 9, 2018

(65) Prior Publication Data
US 2019/0373863 A1 Dec. 12, 2019

Related U.S. Application Data

(60) Provisional application No. 62/452,647, filed on Jan. 31, 2017.

(51) Int. Cl.
*A01K 67/02* (2006.01)
*A01K 67/027* (2006.01)
*A61B 17/02* (2006.01)
*A61K 49/00* (2006.01)

(52) U.S. Cl.
CPC .......... *A01K 67/02* (2013.01); *A01K 67/027* (2013.01); *A61B 17/0293* (2013.01); *A01K 2207/30* (2013.01); *A01K 2227/105* (2013.01); *A01K 2267/03* (2013.01); *A61K 49/0008* (2013.01)

(58) Field of Classification Search
CPC .. A01K 67/02; A01K 67/027; A01K 2207/30; A01K 2227/105; A01K 2267/03; A61B 17/0293; A61K 49/0008
See application file for complete search history.

(56) References Cited

U.S. PATENT DOCUMENTS

| 4,880,217 A | 11/1989 | Navarro, Sr. et al. |
| 5,612,885 A * | 3/1997 | Love ............... A61F 2/2409 345/420 |
| 6,402,780 B2 | 6/2002 | Williamson, IV et al. |
| 8,183,428 B2 * | 5/2012 | Gurtner ............. A61L 15/58 602/50 |
| 8,946,172 B2 | 2/2015 | Mustoe et al. |
| 9,737,523 B2 | 8/2017 | Ghahary et al. |
| 2006/0037091 A1 | 2/2006 | Gurtner et al. |
| 2006/0085035 A1 | 4/2006 | Viola |
| 2015/0157322 A1 | 6/2015 | Elliott et al. |

FOREIGN PATENT DOCUMENTS

WO    9212690 A1    8/1992

OTHER PUBLICATIONS

Aarabi, S., et al.; "Mechanical load initiates hypertrophic scar formation through decreased cellular apoptosis"; FASEB Journal; 21; 3250-3261; 2007.
Le, H., et al.; "Hedgehog signaling is essential for normal wound healing"; Wound Rep Reg; 16; 768-773; 2008.
PCT/US2018/015963; International Search Report and Written Opinion; dated Mar. 23, 2018; 17 pages.

* cited by examiner

*Primary Examiner* — Thaian N. Ton
(74) *Attorney, Agent, or Firm* — Hall Estill Law Firm (57) ABSTRACT

A non-human animal model, method, spring, and kit for testing agents for treating wound scarring. The non-human test animal has a wound in a skin surface thereof, the wound having a perimeter edge; and a garter spring attached to the skin surface of the test animal in a position outside of the perimeter edge of the wound. The garter spring optionally has one or more bands for constricting the force exerted by the coil of the garter spring.

13 Claims, 8 Drawing Sheets

ANIMAL WOUND MODEL AND METHODS OF USE

CROSS-REFERENCE TO RELATED APPLICATIONS

The present application is a national stage application of a PCT application having International Application No. PCT/US2018/015963, filed Jan. 30, 2018, which claims priority to U.S. Provisional Application having U.S. Ser. No. 62/452,647, filed Jan. 31, 2017, which claims the benefit under 35 U.S.C. 119(e), the disclosure of which is hereby expressly incorporated herein by reference.

GOVERNMENT SUPPORT

This invention was made with government support under Contract Number GM060651-10 awarded by the National Institutes of Health. The government has certain rights in the invention.

BACKGROUND

Ideal wound healing would result from fully functional, scar-free healing of wounds. Unfortunately, tens of millions of patients each year suffer from traumatic or burn wounds which lead to dysfunction and/or disfigurement. The dysfunction alone can lead to severe and lifelong disability by means of bony erosion, joint contracture, or loss of limb function. Severe scarring, such as hypertrophic scarring or keloids, can be distressing due to disfigurement even without debilitating loss of function. Human hypertrophic scars are noted to have key features that distinguish them from normal scars (e.g., raised appearance, hyperplasia, abnormal collagen deposition, loss of both rete pegs and hair follicles). The raised appearance, loss of both rete pegs and hair follicles persist in human hypertrophic scars. Understanding the mechanism by which hypertrophic scarring takes place could greatly aid in the development of novel therapeutics for this disease process and other fibrotic disorders. Several current theories exist as to contributing factors to the hypertrophic scarring process, including mechanical tension of the wound, inflammatory response, and bacterial colonization or infection. Mechanical strain on a healing wound in particular is a well-known, long observed and accepted contributor to severe scarring.

A current major barrier to mechanistic investigation of hypertrophic scarring is the lack of an easily reproducible animal model that parallels human hypertrophic scarring. While certain modalities exist to promote hypertrophic scarring in experimental animal models, such as using topical pro-inflammatory mediators, there remains a clear absence of a reproducible experimental animal model which demonstrates the characteristics of human hypertrophic scars. Moreover, the healing of excisional wounds (in which tissue is excised from the site of the wound) is different from that of incisional wounds (in which the wound is due to an incision or cut, but a significant quantity of tissue is not removed).

Gurtner et al. (Pub. No.: US 2006/0037091) teaches an animal model for placing exogenous tension on an incisional wound for producing hypertrophic scarring. The model uses a small palatal expander surgically attached to a longitudinal incisional wound on the test animal. Tension perpendicular to the incision is intermittently increased to create a hypertrophic scar model. Apart from the differences between incisional and excisional wounds, a palatal expander is a large and cumbersome device relative to smaller animal models and is both expensive and technically challenging to surgically attach to the animal. This results in an unsatisfactory rate of unintended early device detachment from the animal. Additionally, palatal expanders are designed so that they are expanded intermittently rather than dynamically. This provides a static mechanical tension to the incisional wound that is increased only at the time of palatal expansion, remaining constant until the next expansion. This is a poor mimic of continuous mechanical tension on a human wound.

Excisional wound models are significantly different from incisional wound models. While incisional wound models are suited more for in situ techniques, excisional wound models enable a more significant wound area, and therefore a larger volume of tissue to be harvested for cells growth and histologic samples. Excisional wounds also allow the study of the rate of contracture after release of splinting, something not possible with incisional wounds. Additionally, excisional wounds, if large enough, can be serially biopsied, allowing healing of a single wound to be studied over a time course. Furthermore, excisional wounds can be covered with occlusive dressings. This allows, if desired, retention of wound exudate for study or the addition of topical pharmaceuticals to the wound itself.

Figure 1:
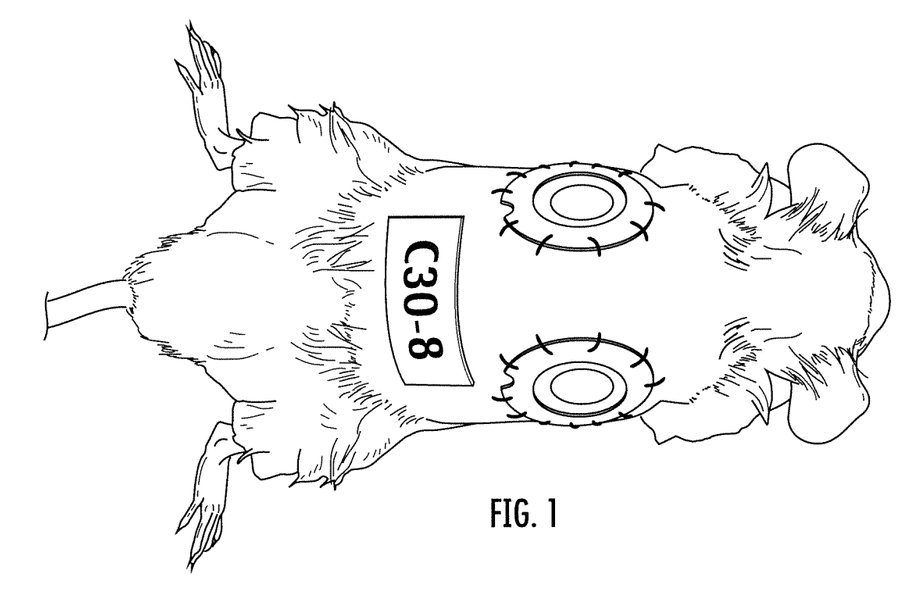
FIG. 1 is a photograph showing a mouse excisional wound model having a pair of silicone rings ("splints") attached to the shaved skin near the perimeters of the wounds (reproduced from "Wound Repair and Regeneration" 16(6):768-73, November, 2008).

Currently available technologies for studying hypertrophic scarring in excisional wound healing involves a simple excisional wound, which is limited by the test animal's wound contracture, and a "splinted" excisional wound having a silicone ring attached to the skin near the perimeter of the wound (e.g., see FIG. 1). Of the two options, the simple excisional wound model has been shown to be inferior to the splinted method (with the silicone ring) at producing hypertrophic scarring due to loose skin and lack of endogenous or exogenous mechanical tension on the wound, allowing for contracture of the wound itself. The splinted wound provides some measure of resistance to wound contracture, but provides no exogenous tension to the excisional wound itself. This lack of exogenous tension on the wound renders the splinted wound model a poor method for producing and examining hypertrophic scarring. It is this deficiency that the novel technology described below, in at least one embodiment, seeks to remedy.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the inventive concepts disclosed herein. The figures are not necessarily to scale and certain features and certain views of the figures may be shown as exaggerated in scale or in schematic in the interest of clarity and conciseness. The patent or application file contains at least one drawing executed in color. Copies of this patent or patent application publication with color drawing(s) will be provided by the Office upon request and payment of the necessary fee.

DETAILED DESCRIPTION

Prior to the present disclosure, there has been no effective animal model in which exogenous mechanical tension is dynamically (continuously) applied to a wound, such as excisional wound. This deficiency is remedied with the novel animal model of hypertrophic wound scarring disclosed herein. In this model, in at least one embodiment, constant exogenous tension is applied to the perimeter of a wound, such as an excisional wound, on a non-human animal. This model is easily reproducible and relatively inexpensive and has particular use in testing agents for use in preventing or treating pathologic scarring during wound healing.

Before further describing various embodiments of the present disclosure in more detail by way of exemplary description, examples, and results, it is to be understood that the embodiments of the present disclosure are not limited in application to the details as set forth in the following description. The embodiments of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. The embodiments of and application and use thereof can be made and executed without undue experimentation in light of the present disclosure. While the present disclosure has been described in terms of particular embodiments, it will be apparent to those of skill in the art that variations may be applied to the apparatus and/or methods and in the steps or in the sequence of steps of the methods described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the apparatus, methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. For example, the range 3 mm to 25 cm therefore refers to and includes all values or ranges of values, and fractions of the values and integers within said range, including for example, but not limited to 4 mm to 22.5 cm, 4 mm to 20 cm, 6 mm to 22 cm, 6 mm to 20 cm, 10 mm to 17 cm, 7.5 nm to 20 cm, 7.5 mm to 10 cm, 5 mm to 16 mm, 4 mm to 20 mm, and 8 mm to 12 cm. Any two values within the range of 3 mm to 25 cm therefore can be used to set the lower and upper boundaries of a range in accordance with the embodiments of the present disclosure.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

The terms "subject" and "patient" are used interchangeably herein and will be understood to refer to a warm blooded animal, particularly a mammal or bird. Non-limiting examples of non-human animals within the scope and meaning of this term, and which can be used in the methods and models described herein, include dogs, cats, rodents (e.g., rats, mice, guinea pigs, hampsters, gerbils), rabbits, pigs, chinchillas, horses, goats, cattle, sheep, zoo animals, Old and New World monkeys, and non-human primates such as apes.

"Treatment" refers to therapeutic treatments. "Prevention" refers to prophylactic treatment measures to stop a condition from occurring. The term "treating" refers to administering a composition to a patient for therapeutic purposes, and may result in an amelioration of the condition or disease.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable biochemical and/or therapeutic effect, for example without excessive adverse side effects (such as toxicity, irritation and allergic response) commensurate with a reasonable benefit/risk ratio when used in the manner of the inventive concepts.

The term "ameliorate" means a detectable or measurable improvement in a subject's condition or or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

Figure 2:
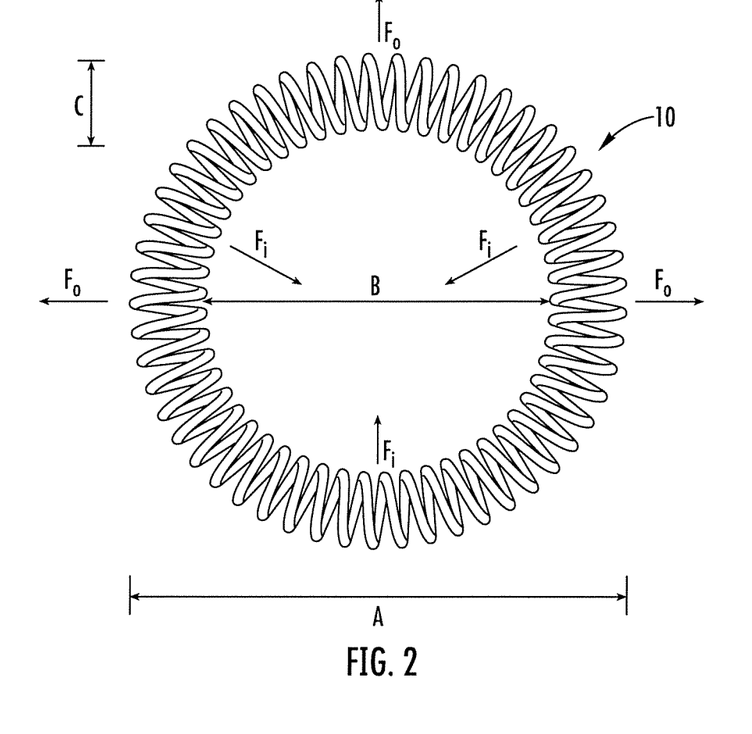
FIG. 2 is a diagram of a garter spring which can be used in accordance with certain embodiments of the present disclosure.

Turning now to the apparatus(es), system(s), and method(s) of the present disclosure, in at least one embodiment, the disclosure is directed to a non-human animal model in which a continuous exogenous mechanical tension is able to be applied by a circular (annular) spring (also referred to herein as a "garter spring") to an excisional (or incisional) wound. A garter spring is a coiled spring that is connected at each end to form a spring having a circular (annular) shape. An example of a garter spring is shown in FIG. 2 and is referred to therein by the general reference numeral 10. Garter spring 10 has an outer diameter A, an inner diameter B, and a coil diameter C. Garter springs are of two types: "compression" and "extension." A compression garter spring exerts outward radial forces away from the center of the spring (represented by arrows $F_o$ in FIG. 2). An extension garter spring exerts inward radial forces toward the center of the spring (represented by arrows $F_i$ in FIG. 2). Compression and extension garter springs such as shown in FIG. 2 can be used in certain embodiments of the present disclosure. U.S. Pat. No. 4,880,217 shows non-limiting examples of garter springs that can be used in certain embodiments of the presently disclosed animal model.

As noted above, silicone ring attachment, as shown in FIG. 1, has been shown to be a technically feasible method of inhibiting wound contracture. However, garter spring attachment as described herein affords the same ease of attachment but with the added benefit of exogenous mechanical tension applied to the wound causing increased hypertrophic scarring. Furthermore, this method of adding exogenous mechanical tension can be adapted to any animal model that requires exogenous mechanical tension. The spring can be attached to the skin by stitches, sutures, ties, adhesives, or any other means effective in attaching or connecting the spring to the skin.

The springs of the present disclosure can be manufactured from any number of materials capable of being a circular garter spring including, but not limited to, stainless steel, carbon steel, and other suitable metals, rubbers, and plastics. Many of these materials can be sterilized and reused, improving cost-effectiveness, or they can be one-use devices. Compression and extension garter springs of the sizes and types described herein are currently able to be produced by a number of manufacturers. Furthermore, changing the size and properties of the manufactured springs allows control of the degree of exogenous mechanical tension (force applied to the perimeter edge), and therefore the degree of scar formation or wound closure (healing).

Outward radial force applied by a compression garter spring of the present disclosure can be varied. The degree of hypertrophic scarring of a wound in the animal model corresponds to the amount of outward radial force applied to the wound by the compression spring. Springs used in the present disclosure can be manufactured with radial forces ranging, for example, from 0-300 Newtons ($(kg)(m/s^{-2})$), such as from about 1 N to about 10 N (e.g., 1, 2, 3, 4, 5, 6, 7, 8, 9, or 10 N), about 10 N to about 20 N (e.g., 10, 11, 12, 13, 14, 15, 16, 17, 18, 19, or 20 N), about 20 N to about 30 N, about 30 N to about 40 N, about 40 N to about 50 N, about 50 N to about 75 N, about 75 N to about 100 N, about 100 N to about 150 N, about 150 N to about 200 N, about 200 N to about 250 N, to about 250 N to about 300 N Increased force applied by the spring on the wound directly increases hypertrophic scarring over the wound.

The springs can be manufactured using a range of coil diameters, inner diameters and outer diameters in order to alter the force applied to the wound and to accommodate wounds of varying sizes and types. Coil diameters such as shown in FIG. 2 as diameter C can vary, for example, over a range of about 0.5 mm to about 50 mm, such as about 0.5 mm to about 10 mm (e.g., 3 mm), about 10 to about 20 mm, about 20 to about 30 mm, about 30 to about 40 mm, or about 40 to about 50 mm. Inner diameters of springs in the non-constricted (i.e., open, non-closed, dynamic) state, such as shown in FIG. 2 as diameter B can vary, for example, over a range of about 3 mm to about 200 mm, such as about 3 mm to about 10 mm (e.g., 4 mm), about 10 mm to about 20 mm, about 20 mm to about 30 mm, about 30 mm to about 40 mm, about 40 mm to about 50 mm, about 50 mm to about 100 mm, to about 100 mm to about 200 mm. Outer diameters of springs in the non-constricted (i.e., open, non-closed) state, such as shown in FIG. 2 as diameter A can vary, for example, over a range of about 4 mm to about 300 mm, such as about 4 mm to about 10 mm, about 10 mm to about 20 mm, about 20 mm to about 30 mm, about 30 mm to about 40 mm, about 40 mm to about 50 mm, about 50 mm to about 100 mm, to about 100 mm to about 300 mm.

In other embodiments, a compression garter spring can be initially provided in a constricted state wherein the outward forces of the spring are maintained in a suspended (static) status by one or more bands that can be cut, detached and/or loosened to enable the spring to exert its outwardly directed forces on a wound. The material used to make the band can be a string, filament, thread, suture, or metal (e.g., stainless steel) or other appropriate material and can be constructed from a natural material (e.g., silk, catgut, string, fiber), or a synthetic material (e.g., nylon, polyglactin, polyglycolic acid, poliglecaprone, polydioxanone, polypropylene, polyamide, or polyester), and may be dissolvable or non-dissolvable. The bands may be "monofilament" or "multifilament" (i.e., braided). The bands may be made of a coated material or an uncoated material. The two ends of the bands may be tied to secure the band in or on the spring, or the two ends of the bands may be fused to secure the band in or on the spring.

Figure 3:
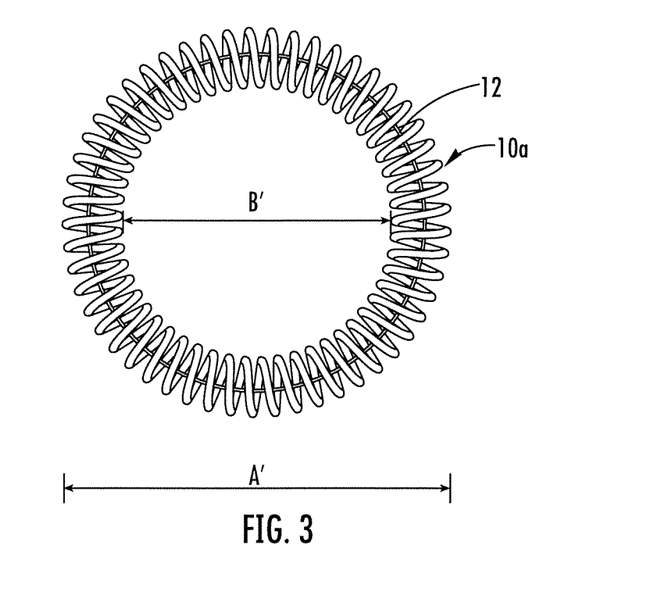
FIG. 3 is a diagram of the garter spring of FIG. 2 is held in a constricted (closed or contracted) position by a band positioned within the coil of the spring. The spring is constricted by the band such that the spring is not exerting an outward or inward force while in the collapsed state.

In one embodiment, shown in FIG. 3, a spring 10a comprises a band 12 within the spring coil which constricts (contracts) the spring 10a to have an outer diameter A' (which is less than the outer diameter A in the non-constricted state shown in FIG. 2) and an inner diameter B' (which is less than the inner diameter B in the non-constricted state shown in FIG. 2). In FIG. 3 the band 12 is shown as a continuous filament, wherein the ends of the band 12 are fused. However, as noted, alternatively the two ends of the band 12 may be tied into a knot to secure the band 12 within the coil of the spring. The outer diameter A' of the spring 10a having the band 12 may be, for example, from 25% to 100% (such as 40% to 75%) of the outer diameter of the spring 10a after the band 12 has severed, thereby releasing the spring 10a from the constricted state shown in FIG. 3. The garter springs used herein can be bound with one or more bands to be constricted in a variety of manners.

Figure 4:
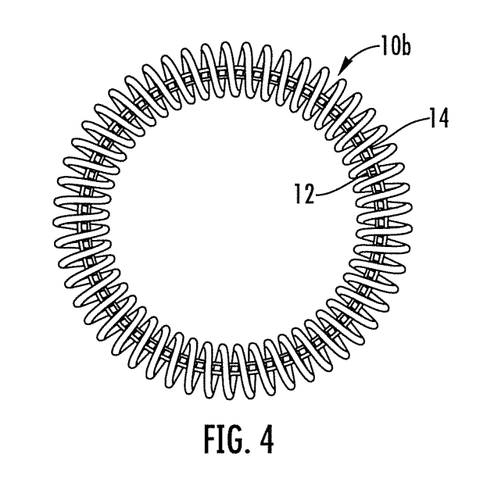
FIG. 4 is a diagram of a garter spring similar to that of FIG. 2 but having two bands within the coil for holding the spring in a constricted state.

In another non-limiting embodiment of the present disclosure, a spring referred to by the reference numeral 10b, shown in FIG. 4, is bound by a first band 12 and a second band 14. The first band 12, which is tighter than the second band 14, constricts (constrains) the spring 10b to have a first inner diameter. When the first band 12 is severed (or loosened) the spring 10b relaxes into a shape constrained by the second band 14, causing the spring 10b to assume a second inner diameter that is greater than the first inner diameter, but is less than the inner diameter of the spring 10b in a fully relaxed state unconstrained by either band 12 or band 14.

Figure 5:
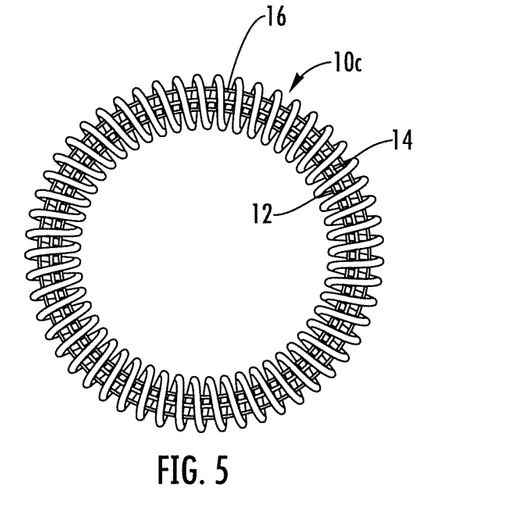
FIG. 5 is a diagram of a garter spring similar to that of FIG. 2 but having three bands within the coil for holding the spring in a constricted state.

In another non-limiting embodiment of the present disclosure, a spring referred to by the reference numeral 10c, shown in FIG. 5, is bound by a first band 12, a second band 14, and a third band 16. The first band 12, which is tighter than the second band 14 and third band 16, constrains the spring 10c to have a first inner diameter. When the first band 12 is severed (or loosened) the spring 10c relaxes into a shape constrained by the second band 14, causing the spring 10c to assume a second inner diameter that is greater than the first inner diameter. When the second band 14 is severed (or loosened) the spring 10c relaxes into a shape constrained by the third band 16, causing the spring 10c to assume a third inner diameter that is greater than the second inner diameter, but is less than the inner diameter of the spring 10c in a fully relaxed state unconstrained by either band 12, 14, or 16.

Figure 6:
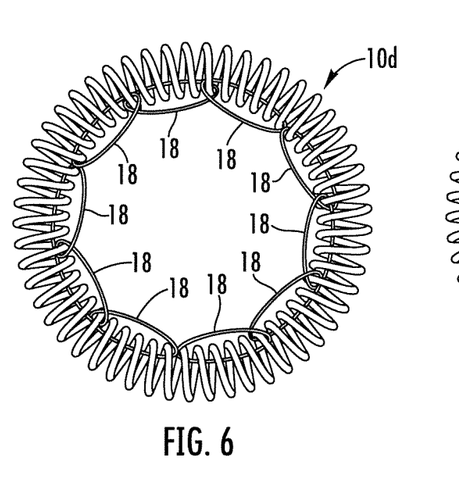
FIG. 6 is a diagram of a garter spring similar to that of FIG. 2 but having a plurality of separate bands outside of the coil for holding discrete adjacent portions of the spring in a constricted state.

In another non-limiting embodiment of the present disclosure, a spring referred to by the reference numeral 10d, shown in FIG. 6, is bound by a plurality of bands 18, each of which binds several adjacent coil loops of the spring 10d causing a subportion of the spring 10d to be constricted to limit the outwardly directed radial force of the spring 10d. When one or more of the bands 18 are severed or loosened, the constraint on the spring 10d is reduced and the compressive force exerted by the spring 10d is increased. When all bands 18 have been severed or loosened, the spring 10d becomes fully relaxed.

Figure 7:
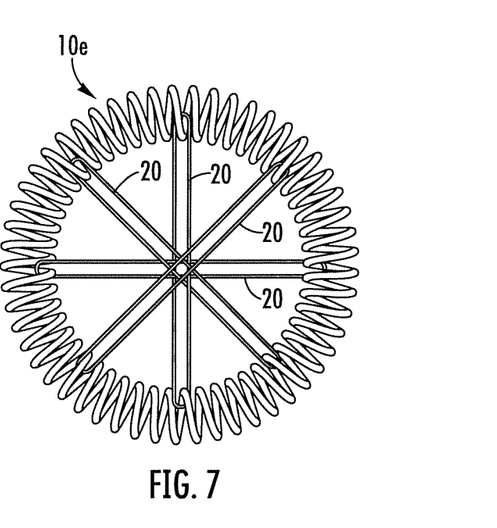
FIG. 7 is a diagram of a garter spring similar to that of FIG. 2 but having a plurality of separate bands outside of the coil for holding discrete opposing portions of the spring in a constricted state.

In another non-limiting embodiment of the present disclosure, a spring referred to by the reference numeral 10e, shown in FIG. 7, is bound by a plurality of bands 20, each of which is attached to opposite coil loops of the spring 10e causing the spring 10d to be constrained to limit the outwardly directed radial force of the spring 10e. When one or more of the bands 20 are severed or loosened, the constraint on the spring 10e is reduced and the compressive force exerted by the spring 10e is increased. When all bands 20 have been severed or loosened, the spring 10e becomes fully relaxed. In other non-limiting embodiments of garter springs of the present disclosure, the garter spring may comprise both bands which are positioned internally within the coil (such as shown in FIGS. 3-5) and bands which are attached externally on portions of the coil (such as shown in FIGS. 6 and 7).

Figure 8A:
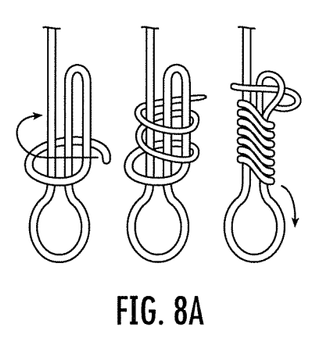
FIG. 8 is a diagrams of knots A-C which can be used in the bands of the garter springs of FIGS. 3-7 for enabling the bands to be secured and/or loosened.
Figure 8B:
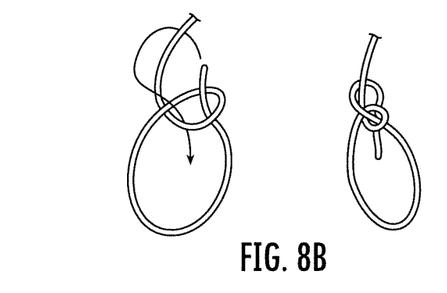
Figure 8C:
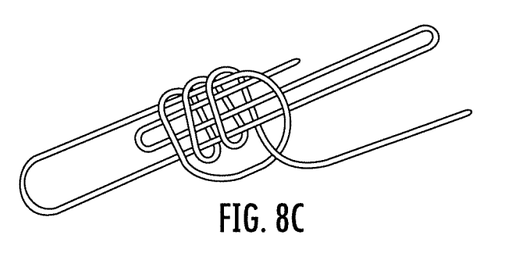

As noted above, the two ends of the bands can be tied rather than fused. Tying the band, in at least certain embodiments, confers the ability to untie, or loosen, the band without having to sever it. Non-limiting examples of how the ends of the band can be tied are shown in FIG. 8A-C. In certain embodiments, the ends of the bands may be tied with a slip knot, a hangman's knot or noose, or a Roedder's knot, which enable the band to be loosened to vary its state of tension.

In use, the garter spring (e.g., springs 10-10e) must be attached to the skin surface of the test animal used in the animal model. The spring can be attached to the skin of the animal either before or after the administration of the wound to the animal. The spring is attached so that it will be outside of the perimeter of the wound. In this way, the outwardly directed force from expansion of a compression spring inhibits wound contracture and provides continuous exogenous tension to the wound, causing more scarring (hypertrophic scarring) than would occur without the spring. In general, the spring has a major diameter which is greater than a major diameter of the wound, wherein a major diameter is defined as the largest distance across the perimeter of a object having a perimeter.

Figure 9:
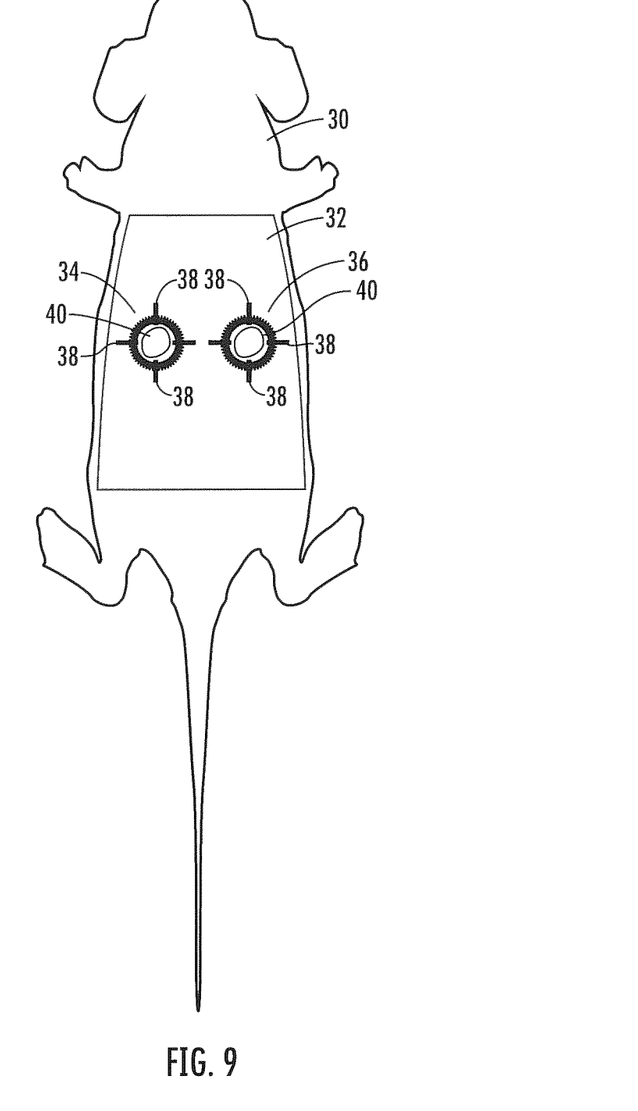
FIG. 9 is a schematic of an animal having a pair of garter springs attached to the skin, each surrounding an excisional wound on the animal.
Figure 10:
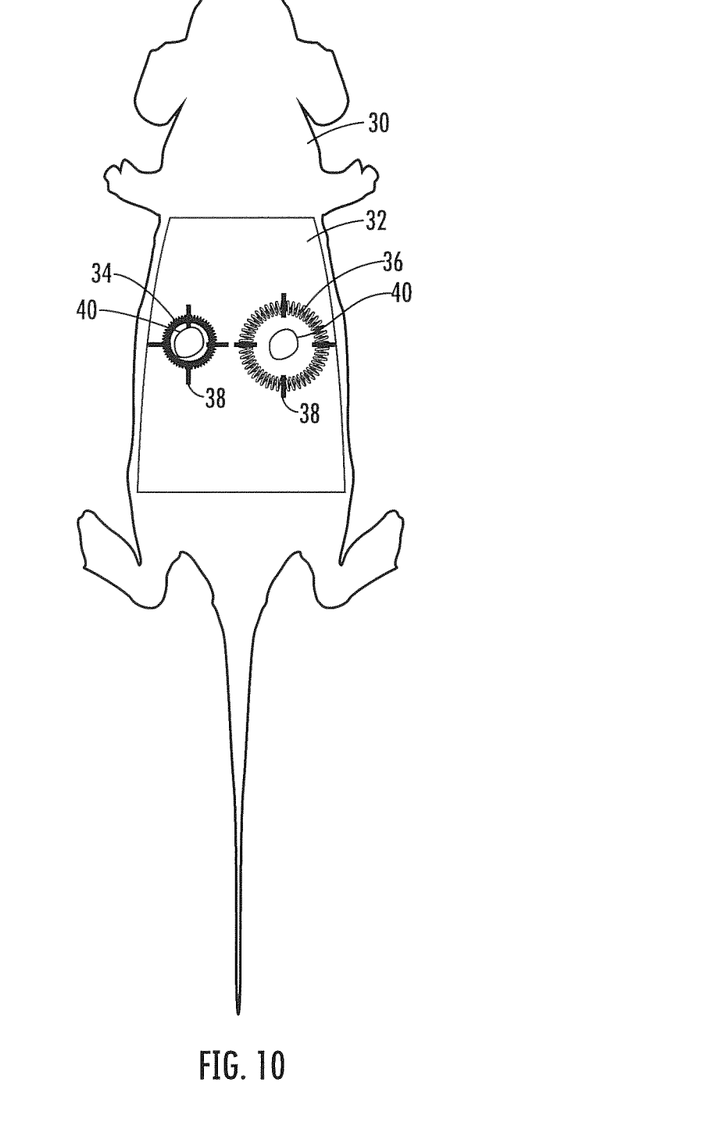
FIG. 10 is a schematic of an animal having a pair of garter springs attached to the skin, each surrounding an excisional wound on the animal. The lefthand spring is constricted with a band, not exerting mechanical tension on wound. The righthand spring has had the band, enabling the spring to exert exogenous tension on the excisional wound.

Usually a pair of springs is attached to the animal (e.g., see FIGS. 9 and 10). Shown in FIG. 9 is a diagram of a mouse 30 having a shaved dorsal surface 32. A pair of garter springs, lefthand spring 34 and righthand spring 36, are attached to the surface 32, such as by a plurality of sutures 38. Each lefthand spring 34 and righthand spring 36 surrounds an excisional wound 40. Four sutures 38 are shown attaching each spring but it will be understood by a person of ordinary skill in the art that any necessary number of sutures, greater than or less than 4 in number can be used depending on the need. In one embodiment the sutures 38 are approximately 2 mm apart. This of course can vary with size of the spring used. The lefthand spring 34 and righthand spring 36 can be selected from (but is not limited to) any one of the spring types shown in FIGS. 2-7. FIG. 10 shows an embodiment wherein in the animal model of FIG. 9, one or more bands such as discussed elsewhere herein has (have) been removed from the righthand spring 36 causing the spring 36 to relax and exert outward radial force on the wound 40.

Additionally, the springs can be placed at multiple time points with respect to wounding procedure. For example, a spring can be in its tension expressing form (open), such as shown in FIG. 2, when it is attached at the time of excisional wounding. Alternatively, as noted, the spring may be attached while constricted with one or more bands (e.g., such as shown in FIGS. 3-7) or other constriction device, wherein there is substantially no mechanical tension (force) on the perimeter edge of the wound at time of placement. In such an embodiment, the spring force is stored as potential energy until the band is released or removed. At this point the spring becomes deployed (opened) and mechanical tension (force) is exerted on the perimeter edge of the excisional wound.

As noted above, springs with a plurality of bands, such as those shown in FIGS. 4-7, can be used in the presently disclosed model. Such an arrangement allows the spring to be readjusted to enable the exertion of varying levels of force during the course of the single use of the model. For example spring 10b of FIG. 4 has three levels of force exertion, a low force level when bands 12 and 14 are both intact, a medium force level, greater than the lowest level, when the band 12 is severed, and a highest force third level, when both bands 12 and 14 have been severed, thereby releasing the spring 10b from constriction.

Due to endogenous mechanical tension of the animal's skin, wound healing in pig skin is the animal model that most closely resembles human wound healing. Thus, models that rely on pigs have been often used for preclinical drug testing for hypertrophic scarring models. However, pigs are difficult to work with and costly to use. The presently disclosed novel model enables companies to test a hypertrophic wound model, such as a hypertrophic excisional wound model, in a higher-throughput, less costly manner, for example in loose-skinned animals, such as but not limited to, rodents and rabbits.

Figure 11:
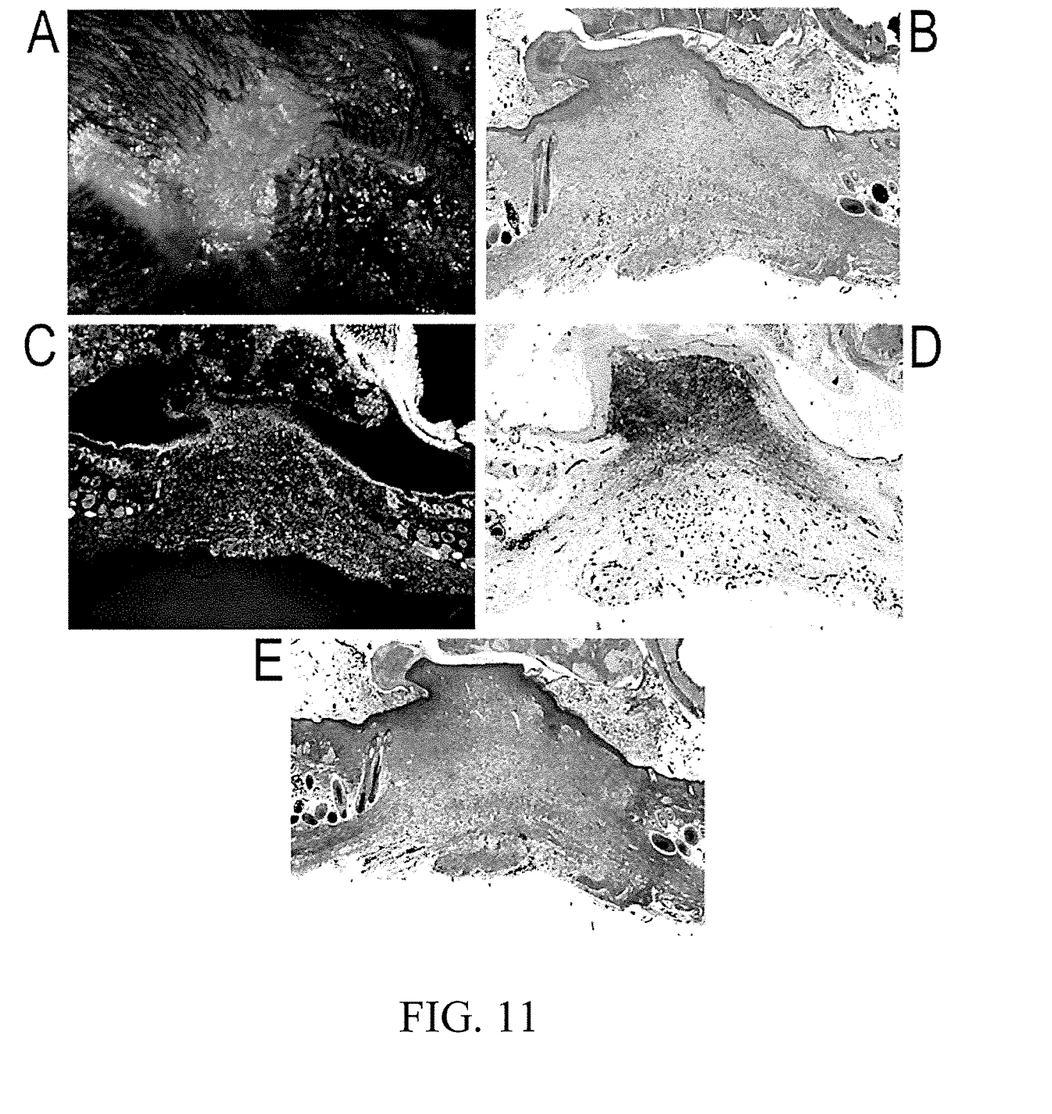
FIG. 11 shows micrographic histological results of the use of a garter spring to exert tension on an excisional wound in a mouse.
Figure 12:
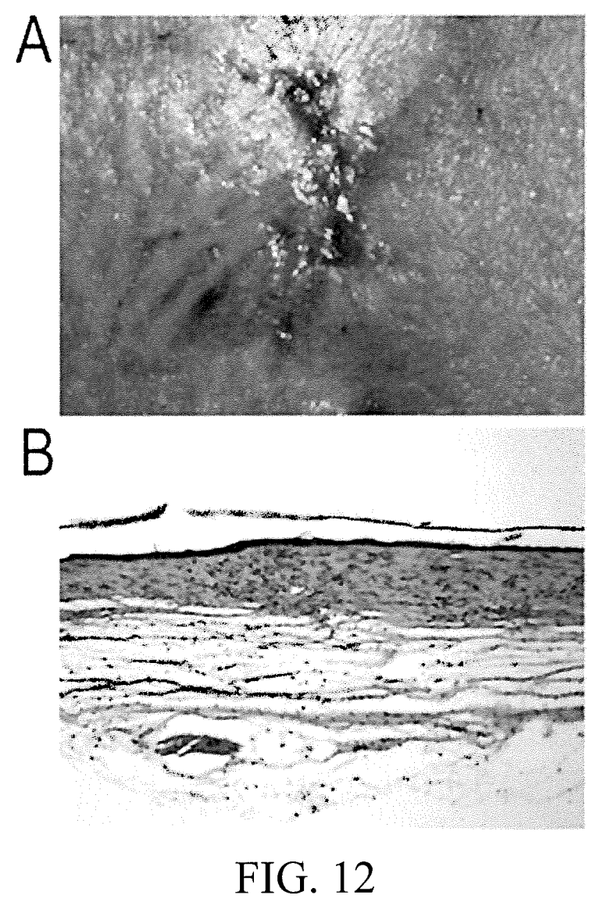
FIG. 12 shows micrographic histological results demonstrating that the hypertrophic scarring that resulted from the model of FIG. 11 was persistent for at least 12 weeks after removal of the garter spring from the test animal.

The excisional wound model, using mice, was used in several experiments which demonstrated that the garter springs resulted in hypertrophic scarring. Results are shown in FIGS. 11A-E and 12A-B. Mice were sutured with a pair of constricted (banded) springs (springs with a single band within the coil, such as shown in FIG. 3). The banded springs surrounded a 6 mm excisional wound. The springs remained constricted for 5 days after which the band was released and the springs exerted force for 5 days at tensions of 4.-5 N-15 N. Representative images of histological sections the mice tissues show that the spring model was capable of producing raised scars that exhibited no hair follicles or rete pegs (FIG. 11A,B). The wound area also showed drastic hyperplasia based on DAPI positive cells in the wound area (FIG. 11C). Lastly, the wound area had an elevated level of SMαA myofibroblasts (FIG. 11D) and abnormal amounts of collagen deposition based on trichrome staining (FIG. 11E). These results are indicative of hypertrophic scarring. The raised appearance (FIG. 12A,B) and loss of both rete pegs and hair follicles (FIG. 12B) were persistent up to 12 weeks post-spring removal. Taken together, the results demonstrate that the use of annular garter springs to produce outward force to an excisional wound is capable of promoting hypertrophic scars that persist and thus the model can be effectively used to be used in experiments involving investigation of wound healing. While in this particular example the spring is attached in the constricted state for 5 days and in the open (non-constricted) state for 5 subsequent days, it will be understood that such durations are merely exemplary and are not limited to such durations and in fact the durations can be selected depending on the particular animal type used, wound size and type, type of spring, type of therapeutic compounds tested, etc. For example, in non-limiting embodiments, the spring in the constricted state, attached to the animal, could be left in the constricted state for 1-20 days, and then in the open state for 1-20 subsequent days (1-20 days/1-20 days), e.g., 1 day/9 days, 2 days/8 days, 3 days/8 days, 3 days/10 days, 4 days/4 days, 4 days/6 days, 5 days/3 days, 5 days/7 days, or 5 days/10 days, to list several purely exemplary examples.

The springs may be made available to the user as part of a kit. The kit includes for example at least one spring (non-constricted, or constricted with one or more bands) such as described elsewhere herein, and at least one of the following items, or more than one of the following items in any combination: suture material, suture needle, needle driver, forecep, hemostat, scissors, biopsy punch (e.g., 6 mm, 7 mm, 8 mm, etc.), hair remover paste, iodine swabs, chloraprep swabs, chest or waist collar to cover the wound, directions for use, and/or a test animal. The chest or waist wound cover collar (e.g., "butterfly collar") may be a piece of fabric or other flexible material sized and shaped to surround a portion of the body of the test animal having the wounds, and which can be secured about the animal via a closure mechanism such as a hook and loop fastener (e.g., VELCRO).

Therefore, in at least certain non-limiting embodiments, the present disclosure is directed to:

Clause 1: A non-human animal model, comprising: a non-human test animal having a wound in a skin surface thereof, the wound having a perimeter edge; and a garter spring attached to the skin surface in a position outside of the perimeter edge of the wound.

Clause 2. The non-human animal model of clause 1, wherein the wound is an excisional wound.

Clause 3. The non-human animal model of clause 1, wherein the wound is an incisional wound.

Clause 4. The non-human animal model of any one of clauses 1-3, wherein the garter spring is constricted in a static position by at least one band.

Clause 5. The non-human animal model of any one of clauses 1-3, wherein the garter spring is in an open, dynamic position such that a force is exerted by the spring on the perimeter edge of the wound.

Clause 6. The non-human animal model of any one of clauses 1-5, wherein the garter spring is a compression garter spring which exerts an outwardly directed force on the perimeter edge of the wound.

Clause 7. The non-human animal model of any one of clauses 1-5, wherein the garter spring is an extension garter spring which exerts an inwardly directed force on the perimeter edge of the wound.

Clause 8. A method of testing an agent for use in treating scarring during wound healing, comprising: obtaining a non-human test animal having a wound in a skin surface thereof, the wound having a perimeter edge, and the non-human test animal having a garter spring attached to the skin surface in a position outside of the perimeter edge of the wound; and applying the agent to the wound of the non-human test animal.

Clause 9. The method of clause 8, wherein the wound is an excisional wound.

Clause 10. The method of clause 8, wherein the wound is an incisional wound.

Clause 11. The method of any one of clauses 8-10, wherein the garter spring is constricted in a static position by at least one band.

Clause 12. The method of any one of clauses 8-10, wherein the garter spring is in an open, dynamic position such that a force is exerted by the spring on the perimeter edge of the wound.

Clause 13. The method of any one of clauses 8-12, wherein the garter spring is a compression garter spring which exerts an outwardly directed force on the perimeter edge of the wound.

Clause 14. The method of any one of clauses 8-12, wherein the garter spring is an extension garter spring which exerts an inwardly directed force on the perimeter edge of the wound.

Clause 15. A kit, comprising: at least one garter spring; and at least one item selected from the group consisting of a suture material, a suture needle, a needle driver, a forecep, a hemostat, a scissors, a biopsy punch, a hair remover paste, an iodine swab, a chloraprep swab, a chest or waist wound cover collar, directions for use, a test animal, and any combination thereof.

Clause 16. The kit of clause 15, wherein the garter spring comprises at least one band within the coil, the at least one band causing a constriction of the garter spring such that the force exerted by the garter spring is less than the force exerted by the garter spring when the at least one band is removed or loosened.

Clause 17. The kit of clause 15, wherein the garter spring comprises at least one band attached to at least two separate portions of the coil, the at least one band causing a constriction of the garter spring such that the force exerted by the garter spring is less than the force exerted by the garter spring when the at least one band is removed or loosened.

Clause 18. A garter spring comprising a coil, and at least one band, wherein the at least one band is positioned within the coil, or is attached to at least two separate portions of the coil, the at least one band causing a constriction of the garter spring such that the force exerted by the garter spring is less than the force exerted by the garter spring when the at least one band is removed or loosened.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims.

What is claimed is:

1. A non-human animal model, comprising:
a non-human test animal having an excisional wound in a skin surface thereof, the wound having a perimeter edge; and
a garter spring attached to the skin surface in a position outside of the perimeter edge of the wound.

2. The non-human animal model of claim 1, wherein the garter spring is constricted in a static position by at least one band.

3. The non-human animal model of claim 1, wherein the garter spring is in an open, dynamic position such that a force is exerted by the spring on the perimeter edge of the wound.

4. A non-human animal model, comprising:
a non-human test animal having a wound in a skin surface thereof, the wound having a perimeter edge; and
a garter spring attached to the skin surface in a position outside of the perimeter edge of the wound, wherein the garter spring is a compression garter spring which exerts an outwardly directed force on the perimeter edge of the wound.

5. The non-human animal model of claim 4, wherein the wound is an excisional wound.

6. The non-human animal model of claim 4, wherein the wound is an incisional wound.

7. The non-human animal model of claim 4, wherein the garter spring is constricted in a static position by at least one band.

8. The non-human animal model of claim 4, wherein the garter spring is in an open, dynamic position such that a force is exerted by the spring on the perimeter edge of the wound.

9. A non-human animal model, comprising:
a non-human test animal having a wound in a skin surface thereof, the wound having a perimeter edge; and
a garter spring attached to the skin surface in a position outside of the perimeter edge of the wound, wherein the garter spring is an extension garter spring which exerts an inwardly directed force on the perimeter edge of the wound.

10. The non-human animal model of claim 9, wherein the wound is an excisional wound.

11. The non-human animal model of claim 9, wherein the wound is an incisional wound.

12. The non-human animal model of claim 9, wherein the garter spring is constricted in a static position by at least one band.

13. The non-human animal model of claim 9, wherein the garter spring is in an open, dynamic position such that a force is exerted by the spring on the perimeter edge of the wound.

* * * * *